(12) United States Patent
Raijmakers et al.

(10) Patent No.: US 7,449,887 B2
(45) Date of Patent: Nov. 11, 2008

(54) STORAGE SPACE FOR ELEMENTS WHICH ARE USED IN A MEDICAL ACTIVITY

(75) Inventors: Jozef H. M. Raijmakers, Eindhoven (NL); Tom P. J. J. Delaey, Eindhoven (NL); Alex Wee Kar Tan, Eindhoven (NL); Laszlo Csaba Herczegh, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 195 days.

(21) Appl. No.: 10/595,987

(22) PCT Filed: Nov. 11, 2004

(86) PCT No.: PCT/IB2004/052384

§ 371 (c)(1),
(2), (4) Date: May 24, 2006

(87) PCT Pub. No.: WO2005/052618

PCT Pub. Date: Jun. 9, 2005

(65) Prior Publication Data

US 2007/0164741 A1    Jul. 19, 2007

(30) Foreign Application Priority Data

Nov. 26, 2003   (EP) .................................. 03104377

(51) Int. Cl.
*G01V 3/00* (2006.01)
(52) U.S. Cl. .................................................... 324/318
(58) Field of Classification Search ......... 324/300–322; 600/410–435
See application file for complete search history.

(56) References Cited

U.S. PATENT DOCUMENTS

| | | | |
|---|---|---|---|
| 5,671,362 A | 9/1997 | Cowe et al. | |
| 5,842,179 A | 11/1998 | Beavers et al. | |
| 5,848,593 A * | 12/1998 | McGrady et al. | 128/897 |
| 5,920,261 A | 7/1999 | Hughes et al. | |
| 6,658,322 B1 * | 12/2003 | Frederick et al. | 700/236 |
| 6,735,497 B2 * | 5/2004 | Wallace et al. | 700/231 |
| 6,785,589 B2 * | 8/2004 | Eggenberger et al. | 700/231 |
| 6,788,997 B1 * | 9/2004 | Frederick | 700/236 |
| 6,963,791 B1 * | 11/2005 | Frederick et al. | 700/244 |
| 6,996,455 B2 * | 2/2006 | Eggenberger et al. | 700/231 |
| 7,258,249 B1 * | 8/2007 | Frederick et al. | 221/282 |
| 7,262,698 B1 * | 8/2007 | Frederick et al. | 340/545.6 |
| 7,263,410 B1 * | 8/2007 | Frederick et al. | 700/236 |
| 7,286,900 B1 * | 10/2007 | Frederick et al. | 700/242 |
| 7,302,164 B2 * | 11/2007 | Wright et al. | 386/95 |
| 7,327,968 B2 * | 2/2008 | Hosoi | 399/81 |
| 2001/0049629 A1 | 12/2001 | Freeman | |
| 2003/0001876 A1 | 1/2003 | Kuang-Shin et al. | |

* cited by examiner

Primary Examiner—Dixomara Vargas

(57) ABSTRACT

Elements (2), which are used in a medical activity, are stored in a storage space (3) including a plurality of partitions (4) which are each dedicated to receiving a certain type of element (2) assigned to a predetermined medical activity. A user interface (6) selects a preferred medical activity from a plurality of medical activities. In response to the input activity, the partition (4) which holds the corresponding element (2) signals to indicate the correct element (2) to be used for the selected activity. In this manner the medical staff is offered 'intelligent' management of medical accessories and space, which helps the staff in organizing elements in an efficient and time-saving manner. In addition, a more flexible working environment contributes to the clinical staff feeling freer at work.

14 Claims, 2 Drawing Sheets

STORAGE SPACE FOR ELEMENTS WHICH ARE USED IN A MEDICAL ACTIVITY

The invention relates to a storage space for elements which are used in a medical activity.

The invention further relates to an element for use with a storage space for elements which are used in a medical activity, an element for use with a MRI-examination device, and a MRI-device using different types of magnetic coils for different examination procedures.

The invention furthermore relates to a method of storing elements which are used in a medical activity.

In view of the increasing number of waiting lists for medical care activities such as operations, there is a pressing need to increase the efficiency of workflow in hospitals.

It is an object of the invention to improve this efficiency of workflow, while providing a pleasant working environment for medical staff.

To achieve this object, a storage space for elements which are used in a medical activity according to the invention, comprising a plurality of partitions which are each dedicated to receiving a certain type of element assigned to a predetermined medical activity, a user interface for selecting a preferred medical activity from a plurality of medical activities, wherein each partition comprises signalling means which provide a signal, dependent on the selected medical activity, to indicate the correct element to be used for the selected activity.

Furthermore, to achieve this object, a method of storing elements which are used in a medical activity according to the invention comprises the steps of providing a plurality of partitions which are each dedicated to receiving a certain type of element assigned to a predetermined medical activity, providing a user interface for selecting a preferred medical activity from a plurality of medical activities and, after selection of a preferred medical activity from a plurality of medical activities, providing a signal via the signalling means of a partition, dependent on the selected medical activity, to indicate the correct element to be used for the selected activity.

In this manner the medical staff is offered 'intelligent' management of medical accessories and space, which helps the staff in organizing elements in an efficient and time-saving manner. A more flexible working environment additionally contributes to the clinical staff feeling freer at work. The invention is further defined by the dependent claims.

Figure 1:
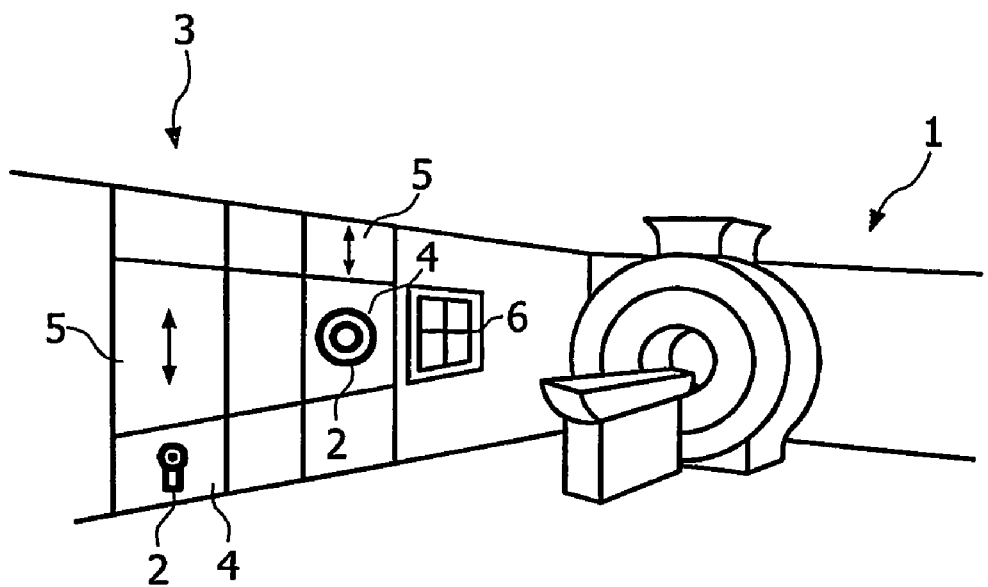
Figure 2:
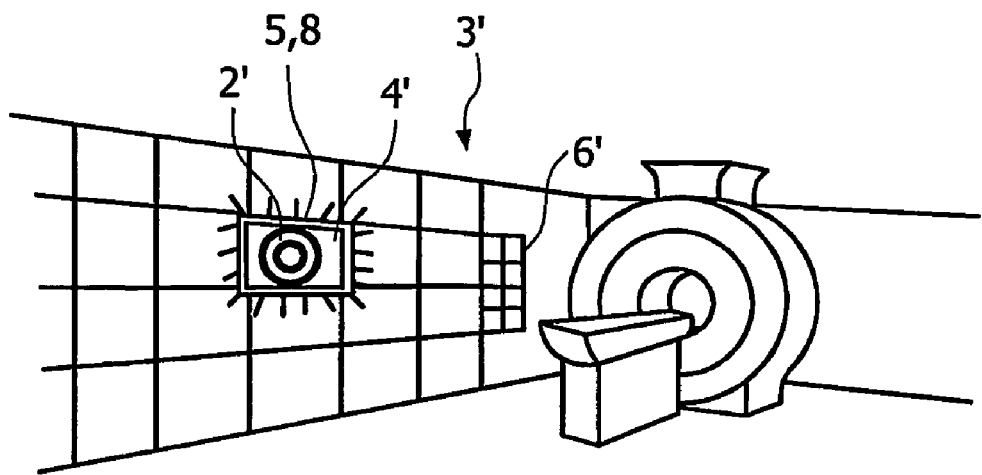
Figure 3:
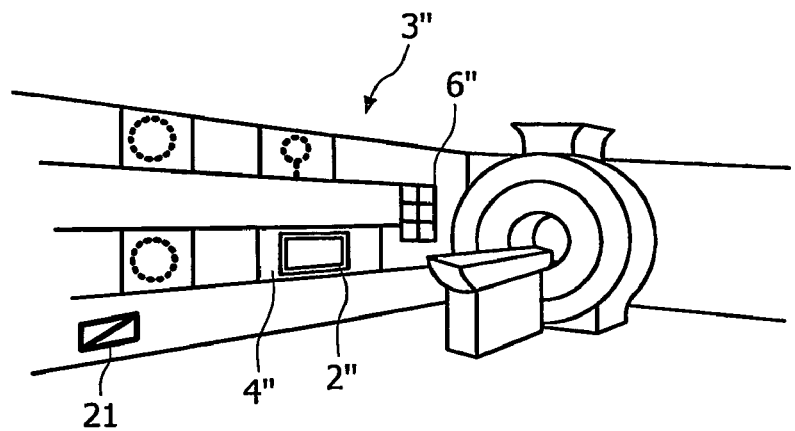
Figure 4:
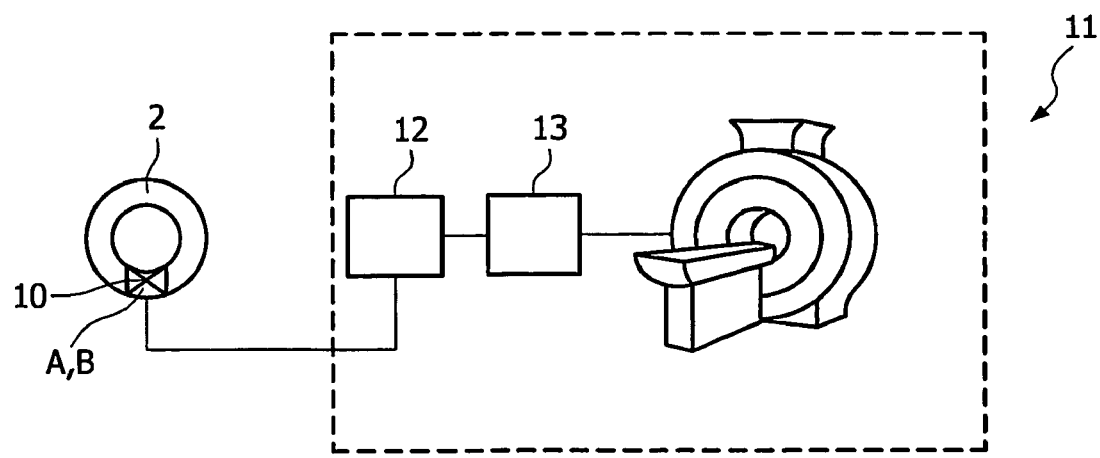

The invention will be described in more detail hereinafter with reference to the drawings, in which:

FIG. 1 shows a first embodiment of a storage space for elements which are used in a medical activity according to the invention, FIG. 2 shows a second embodiment of a storage space for elements which are used in a medical activity according to the invention, FIG. 3 shows a third embodiment of a storage space for elements which are used in a medical activity according to the invention, and FIG. 4 shows an embodiment of a MR-examination device using different types of magnetic coils for different examination procedures, according to the invention.

FIG. 1 shows a first embodiment of a storage space for elements which are used in a medical activity according to the invention. In the described embodiment, the elements comprise magnetic coils, and the medical activity comprises Magnetic Resonance Imaging (MRI). It is noted, however, that the invention is not limited to MRI coils and MRI examination, and that the invention can also be advantageously applied to storage spaces for other types of elements which are used in other medical activities.

In an examination room 1, magnetic coils 2 used for Magnetic Resonance Imaging are stored in a storage space 3, such as for example a cabinet. Each coil 2 has a specific size and shape, dependent on the type of MRI-examination to be carried out. Each coil has its own storage partition 4, and each partition 4 comprises signalling means 5. Furthermore a user interface 6 is provided for selecting a preferred medical activity from a plurality of medical activities. The user interface 6 comprises means for selecting a medical activity from a plurality of medical activities, said means being chosen from a group including voice control, touch screen, buttons, computer keyboard. It is noted that this user interface 6 may be comprised in the storage space 3 itself, but also for example in a wall of the examination room, or even outside the examination room, in a control room, as long as it is connected to the storage space 3.

Before an MRI-examination procedure starts, a member of the medical staff selects a preferred MRI-examination from a plurality of varying types of MRI-examination, for example MRI of the head of a patient. A control unit receives the information on the selected type of examination via the user interface 6, and accordingly activates the signalling means 5 of the partition which contains the correct MRI-coil. Dependent on the selected MRI-examination, the signalling means 5 comprised in the partition which contains the correct MRI-coil then provides a signal to the staff member to indicate the correct element to be used for the selected activity, in this case the specific coil for MRI of the head. It is noted that dependent on the selected MRI-procedure, also the signalling means comprised in more than one partition can be activated, when more than one coil is needed for that specific examination. In this embodiment, the provided signal indicates the opening of a door 7 which reveals the coil 2 to be used.

The medical staff member will then take out the correct coil, place it in the MRI-examination device, and carry out the examination. In this manner, there is a higher efficiency in selecting the correct coil, because the medical staff member only has to indicate the preferred procedure, and does not have to remember, or look up, which coils are to be used. Thus the efficiency of workflow of the medical staff is improved, while a pleasant working environment for medical staff is provided. Furthermore, this diminishes the risk of choosing a wrong type of coil for a certain MRI-examination.

In the embodiment in FIG. 1, moving doors are shown as an embodiment of signalling means. The door covering the relevant coil is opened upon selection of a certain procedure. However, other types of visual signals can also be applied, as shown in FIG. 2.

FIG. 2 shows a second embodiment of a storage space 3' for elements which are used in a medical activity according to the invention. In the described embodiment, each partition 4' is provided with a lighting device 8 as the signalling means, which is activatable through the selection of the medical activity by a user. Besides visual signals, the signalling means may be arranged to provide also audio signals. The audio signals may differ dependent on the type of coil needed for the examination.

It is furthermore advantageous if an element 2 for use with the storage space 3 comprises an identifier with data A relating to storage partition location, which data are readable by reading means 21 provided in the storage space 3 for identifying the correct partition 4 to store the element via the signalling means 5. After finishing the examination procedure, the data in the identifier in the used coil are read by the reading means in the storage space when the coil is brought in the vicinity of the storage space. Then the signalling means 5 comprised in the correct partition 4 are activated by the control unit, and the relevant partition is for example lighted up via the activated lighting means. Thus the coil can easily be stored in its correct partition after use. This further enhances the efficiency of the workflow. In this manner the coils could even be placed back in the storage space by other persons than the specifically trained medical staff, which gives them more time to do other things, and prepare for example a next examination.

FIG. 3 shows a further embodiment of a storage space, 3" for elements which are used in a medical activity according to the invention. In the described embodiment, each partition 4" is provided with a glass covering, which glass covering is interchangeable between transparent and opaque. In the rest position of the storage space 3", all glass coverings are opaque. Upon selection by a medical staff member of a certain examination procedure, the partition 4" with the correct coil 2" becomes transparent and reveals the coil to be used.

FIG. 4 furthermore shows schematically a MRI-examination device 11 using different types of magnetic coils for different examination procedures, wherein the device 11 comprises reading means 12 for reading data B into an identifier 10 which is comprised in each coil 2, and means 13 for indicating a correct position of said coil 2 relative to the device 11 for the specific examination procedure, based on the data B in the identifier.

The identifier 10, as described before, furthermore comprises data B relating to element position relative to the device 11, which data are readable by reading means 12 provided in the examination device 11, for identifying a correct position of the element 2 relative to the device 11 for the specific examination procedure, based on the data in the identifier 10, via the indicating means 13. This is advantageous because in this manner the positioning of the coil relative to the device does not have to rely only on the eye of the medical staff member.

It is noted that the identifier 10 may comprise only data B relating to the position of the element relative to the device in itself, i.e. it does not comprise data A relating to storage partition location. It is advantageous if the identifier comprises an identifier chosen from a group consisting of radio frequency transponders and barcodes, and the reader comprises a reader chosen from a group consisting of radio frequency readers and barcode readers. However, it is noted that also other known types of identifier-technologies can be advantageously applied.

In an examination room MR-coils are stored in a cabinet such that each coil has its own place with a clear visual indication. After selection of a certain procedure the needed coil(s) are indicated (eg. through lighting up of this coil or the cabinet partition where this coil is stored). In an embodiment the coil is provided with a Radio-Frequency-identifier so that the system linked to the cabinet recognizes whether it is replaced in the right partition. In the MR-magnet the coil can also be positioned through location recognition with the RF-ID.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A storage space for elements which are used in a medical activity, comprising:
   a plurality of partitions which each are dedicated to receiving a certain type of magnetic coils assigned to a predetermined Magnetic Resonance Imaging activity's,
   a user interface for selecting a magnetic resonance imaging activity from a plurality of magnetic resonance imaging activities,
   wherein each partition comprises signaling means which provide a signal, dependent on the selected magnetic resonance imaging activity, to indicate the correct magnetic resonance imaging coil to be used for the selected magnetic resonance imaging activity.

2. The storage space as claimed in claim 1, wherein the signaling means provide visual signals.

3. The storage space as claimed in claim 2, wherein each partition is provided with a lighting device, which is activatable through the selection of the magnetic resonance imaging activity by a user.

4. The storage space as claimed in claim 1, wherein the signaling means provide audio signals.

5. The storage space as claimed in claim 1, wherein the user interface comprises means for selecting the magnetic resonance imaging activity from a plurality of magnetic resonance imaging activities, said means being chosen from a group including voice control, touch screen, buttons, computer keyboard.

6. The storage space as claimed in claim 1, wherein the storage space comprises reading means for reading data which are provided in an identifier which is comprised in each element magnetic coil to be stored in the storage space, and control means for controlling the signaling means for indicating the correct partition to store the magnetic resonance imaging coil, based on the data in the identifier.

7. A magnetic resonance imaging coil for use with a storage space as claimed in claim 6, wherein the element magnetic resonance imaging coil comprises an identifier with data relating to storage partition location, which are readable by reading means provided in the storage space, for identifying the correct partition to store the magnetic resonance imaging coil via the signaling means.

8. A storage space as claimed in claim 1, wherein each coil includes a coil identifier and further including:
   reading means for reading data from the coil identifier of each coil, and
   means for indicating a correct position of a selected one of the coils relative to an MM device for a selected examination procedure, based on the data in the identifier.

9. A method of storing elements which are used in a medical activity, comprising the steps of:
   providing a plurality of partitions which each are dedicated to receiving a certain t e of clement assigned to a predetermined medical activity,
   providing a user interface for selecting a preferred medical activity from a plurality of medical activities, and
   upon selection of a preferred medical activity from a plurality of medical activities, providing a signal, dependent on the selected medical activity, to indicate the correct element to be used for the selected activity, wherein the elements include insertable magnetic resonance imaging coils.

10. The method as claimed in claim 9, further including:
    when an element is brought to the partitions for storage, sensing an element identification;
    signaling a corresponding one of the partitions in accordance with the sensed element identification.

11. A storage system for storing coils which are used in magnetic resonance activities, the storage system comprising:
- a plurality of partitions, each configured to store a corresponding coil;
- an interface through which a user designates a selected magnetic resonance activity;
- a visual indicator device which provides a visible indication of a partition configured to hold the corresponding coil to be used in the selected med-teal magnetic resonance activity.

12. The storage system as claimed in claim 11, wherein the elements coils include electrically readable identifiers and further including:

- an electronic identification reader configured to read the electric identifier of a one of the coils to be stored, the visual indicator device providing the visible indication of the partition configured to store the identified element coil.

13. The storage system as claimed in claim 11, wherein the coils include magnetic resonance imaging coils.

14. The storage system as claimed in claim 13, wherein the interface is an MRI interface through which the user sets a scan procedure for an MRI scanner.

\* \* \* \* \*